US010098932B2

(12) United States Patent
Kleiner-Fisman (10) Patent No.: US 10,098,932 B2
(45) Date of Patent: Oct. 16, 2018

(54) BOTULINUM TOXIN FOR USE IN THE TREATMENT OF PARATONIA (71) Applicant: Galit Kleiner-Fisman, Toronto (CA)

(72) Inventor: Galit Kleiner-Fisman, Toronto (CA)

( * ) Notice: Subject to any disclaimer, the term of this patent is extended or adjusted under 35 U.S.C. 154(b) by 0 days.

(21) Appl. No.: 15/316,324

(22) PCT Filed: Jun. 5, 2015

(86) PCT No.: PCT/CA2015/000363
§ 371 (c)(1),
(2) Date: Dec. 5, 2016

(87) PCT Pub. No.: WO2015/184528
PCT Pub. Date: Dec. 10, 2015

(65) Prior Publication Data
US 2017/0143808 A1 May 25, 2017

(30) Foreign Application Priority Data
Jun. 6, 2014 (EP) ..................... 14001978

(51) Int. Cl.
A61K 38/48 (2006.01)
A61K 9/00 (2006.01)
A61K 47/02 (2006.01)

(52) U.S. Cl.
CPC ........ A61K 38/4893 (2013.01); A61K 9/0019 (2013.01); A61K 47/02 (2013.01); C12Y 304/24069 (2013.01)

(58) Field of Classification Search
None
See application file for complete search history.

(56) References Cited

PUBLICATIONS

Lam, Kuen; et al; "Can Botulinum Toxin Decrease Carer Burden in Long Term Care Residents With Upper Limb Spasticity? A Randomized Controlled Study" JAMDA, 13, 477-484, 2012 (Year: 2012).*
Vahia, Ipsit; et al; "Prevalence and Impact of Paratonia in Alzheimer Disease in a Multiracial Sample" The American Journal of Geriatric Psychiatry, 15, 351-353, 2007 (Year: 2007).*
International Search Report dated Aug. 3, 2015 in connection with PCT international application No. PCT/CA2015/000363.
Written Opinion of the International Searching Authority dated Aug. 3, 2015 in connection with PCT international application No. PCT/CA2015/000363.
Kleiner-Fisman et al., 2014, "A Randomized, Placebo Controlled Pilot Trial of Botulinum Toxin for Paratonic Rigidity in People with Advanced Cognitive Impairment," PLoS One 9(12):e114733.
Hobbelen et al., 2008, "Diagnosing paratonia in the demented elderly: reliability and validity of the Patatonia Assessment Instrument (PAI)," Int Psychogeriatr. 20(4):840-52.
Hobbelen et al., 2006, "Paratonia: a Delphi Procedure for Consensus Definition," J Geriatr Phys Ther. 29(2):50-6.

(Continued)

Primary Examiner — David W Berke-Schlessel
(74) Attorney, Agent, or Firm — Biospark Intellectual Property Law (57) ABSTRACT The present invention relates to botulinum toxins for use in the treatment of paratonia. In particular, the present invention relates to the treatment of paratonia by local administration of a botulinum toxin to a muscle of a patient.

18 Claims, 3 Drawing Sheets (56) References Cited

PUBLICATIONS

Aprile et al., 2015, "Pain in stroke patients: characteristics and impact on the rehabilitation treatment. A multicenter cross-sectional study," Eur J Phys Rehabil Med. 51:725-36.
Connolly and Lang, 2014, "Pharmacological Treatment of Parkinson Disease A Review," JAMA 311(16):1670-1683, doi:10.1001/jama.2014.3654, downloaded on Mar. 27, 2018.
Hobbelen et al., 2012, "Passive movement therapy in severe paratonia: a multicenter randomized clinical trial," Int Psychogeriatr. 24(5):834-844.
Marinelli et al., 2017, "Electromyographic assessment of paratonia," Exp Brain Res. 235(3):949-956.
Souren et al., 1997, "Neuromotor Changes in Alzheimer's Disease: Implications for Patient Care," J Geriatr Psychiatry Neurol. 10:93-8.

\* cited by examiner

BOTULINUM TOXIN FOR USE IN THE TREATMENT OF PARATONIA

FIELD OF THE INVENTION

The present invention relates to botulinum toxins for use in the treatment of paratonia. In particular, the present invention relates to the treatment of paratonia by local administration of a botulinum toxin to a muscle of a patient.

BACKGROUND OF THE INVENTION

Dementia is often assumed to be a disorder only of cognitive impairment, however, it is often accompanied by significant motor disability due in part to "paratonia", a form of increased muscle tone. First observed by Dupre in 1910 (Dupre, E., Rev. Neurol. 1910; 20:54-56), it was characterized as "an inability to relax muscles in the setting of cognitive impairment". Paratonia exerts its effects by increasing muscle resistance reflexively when a limb is moved passively, though can fluctuate in severity depending on level of relaxation. In advanced dementia, increased tone may also exist at rest and maintains muscle in a prolonged shortened state leading to fixed postures (contractures). Paratonia has been estimated to be present in 5% of those with mild cognitive impairments and 100% in those with advanced dementia (see, e.g., Hobbelen et al., Int. Psychoger. 2008, 20:840-852; Franssen et al., Arch. Neurol. 1993, 50:1029-1039; Souren et al., J. Geriatr. Psychiatry Neurol. 1997, 10:93-98; and Hobbelen et al., BMC Geriatr. 2007, 7:30).

Some of the consequences of fixed postures include difficulties in washing, dressing, feeding, and providing general care to a fully dependent person increasing caregiver burden. Contractures often lead to skin breakdown, infection, and pain upon movement, thereby reducing comfort and quality of life. Once contractures have developed, medical treatments are generally futile. However, contractures may be avoided or delayed, if paratonia is recognized and treated.

Botulinum toxins, in particular botulinum toxin type A, have been widely used to address hypertonic states such as dystonia, for example cranial dystonia (e.g., blepharospasm, oromandibular dystonia), cervical dystonia (e.g., spasmodic torticollis) and laryngeal dystonia (e.g., spasmodic dysphonia), and spasticity (e.g., post-stroke spasticity). Botulinum toxin is an exotoxin produced by the bacterium *Clostridium botulinum* that specifically binds to presynaptic cholinergic nerve terminals and inhibits the release of the neurotransmitter acetylcholine in a dose-dependent manner (Kao et al., Science 1976, 193:1256-1258). This results in local paralysis and hence relaxation of the muscles afflicted by the hypertonic state such as dystonia and spasticity. Injections of botulinum are generally well tolerated, have minimal side-effects, and are effective for approximately 3 months with peak effect occurring after about 4 to 6 weeks.

Currently, the main therapy for paratonia is the passive movement therapy (PMT), which aims to decrease high muscle tone and to sustain range of motion of the affected joints. However, there are general doubts about the beneficial effects of this widely used therapy. It was observed that the frail elderly patients, who often show signs of discomfort during the treatment, are prone to injury and not able to actively use regained mobility. In fact, a pilot study with PMT even showed an increased muscle tone in the PMT group, as compared to controls, indicating a possible association with muscle fibre injuries (Hobbelen et al., Nederlands Tijdschrift voor Fysiotherapie 2003, 113:132-137). A later multi-centre randomized controlled trial to assess the efficacy of PMT in dementia patients with paratonia showed that PMT has no beneficial effects on the muscle tone but shows a trend towards worsening of joint and limb stiffness compared with controls. PMT was therefore not recommended as an intervention in severe paratonia (Hobbelen et al., Int. Psychogeriatr. 2012, 24:834-844).

Thus, no effective treatment is currently available for patients afflicted with paratonia such that activities of daily living (ADLs) could be facilitated and discomfort and consequences of immobility could be delayed or prevented.

SUMMARY OF THE INVENTION

The present disclosure relates to a botulinum toxin for use in the treatment of paratonia. In some embodiments, for example, the paratonia is a form of hypertonia that is different to, and can be distinguished from, Parkinsonian rigidity and spasticity.

Further embodiments, in particular with regard to the dose and mode of administration, are set forth herein.

In a first embodiment, a botulinum toxin for use in the treatment of paratonia is provided.

The botulinum toxin for use according to the first embodiment, wherein the paratonia has been diagnosed to have a PAI (paratonia assessment instrument) score of ≥3, is provided in a second embodiment.

The botulinum toxin for use according to the first or second embodiment, wherein the paratonia affects an upper and/or lower limb, is provided in a third embodiment.

The botulinum toxin for use according to any one of the first to third embodiments, wherein the paratonia is associated with cognitive impairment as a result of Alzheimer's disease (AD), vascular dementia (VaD), dementia with Lewy bodies (DLB), frontotemporal dementia (FTD), subcortical vascular dementia (SVD), or mixed dementia not otherwise specified (NOS), is provided in a fourth embodiment.

The botulinum toxin for use according to any one of the first to fourth embodiments, wherein the botulinum toxin is locally administered by intramuscular injection, is provided in a fifth embodiment.

The botulinum toxin for use according to any one of the first to fifth embodiments, wherein the botulinum toxin is administered in an amount of about 10 to 700 Units, is provided in a sixth embodiment.

The botulinum toxin for use according to any one of the first to sixth embodiments, wherein the botulinum toxin is selected from the group consisting of botulinum toxin types A, B, $C_1$, D, E, F, G, and mixtures thereof, is provided in a seventh embodiment.

The botulinum toxin for use according to the seventh embodiment, wherein the botulinum toxin is botulinum toxin type A, is provided in an eighth embodiment.

The botulinum toxin for use according to any one of the first to eighth embodiments, wherein the botulinum toxin is a botulinum toxin complex or the neurotoxic component of a botulinum toxin complex, is provided in a ninth embodiment.

In a tenth embodiment, a method of treating paratonia in a patient, the method comprising locally administering a therapeutically effective amount of botulinum toxin to a muscle of the patient is provided.

The present disclosure may be more fully understood by reference to the following detailed description of the present invention, the example, and the accompanying drawings.

DETAILED DESCRIPTION OF THE INVENTION

The present invention is based on the surprising finding that botulinum toxin treatment provides a safe and efficacious treatment option to reduce paratonia in a patient, in particular in cognitively impaired, elderly people with advanced dementia. Specifically, it was found that administration of botulinum toxin, e.g., by intramuscular injection, can increases the range of motion and reduce involuntary postures. This facilitates the activities of daily living (ADLs) and reduces the patient's discomfort. In particular, it was unexpectedly found that the toxin treatment produced significant improvement in the caregiver burden scale (CBS) and, thus, can reduce caregiver burden in people with paratonic rigidity.

In some embodiments, the individuals to be treated are generally individuals with both cognitive impairment (dementia) and paratonia, in particularly elderly frail individuals with advanced dementia and paratonia. The cognitive impairment of the patients with paratonia treated in accordance with the present invention may, in some embodiments, be the result of Alzheimer's disease (AD), vascular dementia (VaD), dementia with Lewy Bodies (DLB), frontotemporal dementia (FTD), subcortical vascular dementia (SVD), or mixed dementia not otherwise specified (NOS). In some embodiments, the paratonia to be treated within this invention may be characterized or defined by having a PAI (paratonic assessment instrument) score of ≥3.

The botulinum toxin used in the treatment of paratonia, in some embodiments, is not particularly limited and embraces all known serotypes (i.e., types A, B, C, D, E, F and G) and subtypes thereof of either the toxin complex (i.e. the neurotoxic polypeptide in complex with additional, so-called "non-toxic" proteins) or the neurotoxic component (i.e. the neurotoxic ("150 kDa") polypeptide without any "non-toxic" or "complexing" proteins).

In a first aspect, the present invention relates to a botulinum toxin for use in the treatment of paratonia. The term "treatment", as used within the context of the present invention, broadly relates to any method used to alleviate, delay onset, or reduce severity or incidence of a disease, disorder or condition, or symptom thereof.

The term "paratonia", as used herein, generally refers to a form of hypertonia with an involuntary variable resistance during passive movement. For example, attempting to move a limb of a person afflicted with paratonia generally results in the person involuntarily resisting the movement (aka "Gegenhalten"). The degree of resistance generally varies depending on the speed of movement (e.g., a lower resistance to slow movement and a high resistance to fast movement), and the degree of paratonia is generally proportional to the amount of force applied. Furthermore, the resistance to passive movement is generally in any direction and there is generally no clasp-knife phenomenon.

Furthermore, it is pointed out that, within the present invention, the term "paratonia" is intended to refer to a defined state, condition or disease, which is distinct to, and does not overlap with, other neurodegenerative disorders. In particular, paratonia differs from spasticity and Parkinsonian (aka "lead-pipe") rigidity. In the context of the present invention, the term "spasticity" may be defined as a motor disorder characterized by velocity dependent increase in the tonic stretch reflex with exaggerated tendon jerks, and the term Parkinsonian rigidity may be defined as a resistance to passive movement of the limb whereby the degree of resistance is constant whether the limb is moved slowly or rapidly (like bending a lead pipe).

Thus, within the framework of the present invention, paratonia can be distinguished from spasticity by, for example, observing a lack of exaggerated deep tendon reflexes and/or a lack of clasp-knife response. Further, paratonia can be distinguished from Parkinsonian rigidity, for example, in that the amount of resistance in Parkinsonian rigidity does not vary with the velocity of the movement. Thus, the botulinum toxin used herein is generally for use in the treatment of paratonia that is neither associated with spasticity nor with Parkinsonian rigidity, or for administration to a patient having paratonia but neither suffers from spasticity nor from Parkinsonian rigidity.

The underlying cause for the development of paratonia is not known. However, the underlying pathology is generally considered to be different to that of spasticity and Parkinsonian rigidity. Paratonia is an independent (or separate) condition which, in particularly in advanced stages, itself contributes to the cause of the decline of functional mobility observed in people afflicted with dementia.

Within the context of the present invention, the paratonia to be treated is not limited to a particular stage or severity. As noted above, paratonia is generally observed in the setting of cognitive impairment like dementia, and its severity generally increases with progression of dementia. In other words, the nature of paratonia typically changes with progression of the dementing illness. While paratonia exerts its effects by increasing muscle resistance reflexively when a limb is moved passively, in advanced dementia, increased tone may also exist at rest and maintains muscle in a prolonged shortened state leading to fixed postures (contractures).

For example, active assistance (aka "Mitgehen") is more common early in the course of degenerative dementia, whilst active resistance is more common later in the course of the disease. It is contemplated that the present invention addresses all these different stages or degree of severity of paratonia. However, the botulinum toxin treatment of the present invention is particularly useful for treating patients with moderate to severe dementia, in particular elderly people with moderate to severe dementia and/or patients (e.g. elderly patients) with advanced dementia and paratonia having involuntary postures that interfere in the ability to provide care and/or cause patient suffering.

In some embodiments, the botulinum toxin treatment of the present invention addresses later stages of paratonia diagnosed using the Paratonia Assessment Instrument (PAI). Specifically, the paratonia to be treated has preferably been diagnosed to have a PAI score of ≥3, more preferably ≥4. In individuals with a severity corresponding to a PAI of ≥3 or ≥4, the paratonia typically results in involuntary postures interfering in care, compromising comfort and/or increasing caregiver burden.

The PAI is a reliable assessment tool for diagnosing paratonia and to distinguish it from Parkinson's rigidity and spasticity after stroke (Hobbelen et al., Int. Psychogeriatr. 2008, 20:840-852). Paratonia is diagnosed when the following criteria are fulfilled: 1) there is an involuntary variable resistance; 2) the degree of resistance varies depending on the speed of movement (e.g. a low resistance by slow movement and a high resistance by fast movement; 3) the resistance to passive movement can be in any direction; 4) there is no clasp-knife phenomenon; and 5) the resistance is felt in two movement directions in one limb or in two different limbs.

In some embodiments of the present invention, the paratonia to be treated herein may be a paratonia affecting an upper and/or lower limb, especially the legs and/or arms. In some embodiments, for example, the upper limb muscle affected by paratonia chosen for administration of botulinum toxin may be selected from, among others, biceps brachii, brachioradialis, pectoralis major, flexor digitorum superficialis, flexor digitorum profundis, flexor pollicis longus, triceps, lumbricals, flexor carpi ulnaris, and opponens pollicis. In some embodiments, for example, the upper limb muscles lead to posture problems.

In some embodiments, for example, the lower limb muscle affected by paratonia chosen for administration of botulinum toxin may be selected from, among others, hamstrings, quadriceps, adductor longus, adductor magnus, gastrocnemius, flexor digitorum longus, tibialis posterior, flexor hallucis longus, extensor digitorum longus, extensor hallucis longus, tibialis anterior, flexor digitorum brevis, extensor digitorum brevis and iliopsoas.

In accordance with the present invention, the patient to be treated within the present invention (the target patient(s) or patient group) is generally an individual that has paratonia as a complication of cognitive impairment (i.e. dementia). The term "dementia", as used herein, generally relates to any loss of mental ability severe enough to interfere with normal activities of daily living. Within the present invention, "dementia" may be diagnosed according to the Diagnostic Statistical Manual IV-TR criteria (Diagnostic and statistical manual of mental disorders: DSM IV, 4th ed., Washington D.C.: American Psychiatric Association, 1994). Whilst paratonia was also observed in patients with mild dementia (i.e. at an early stage of dementia), the present invention, in some embodiments, aims at treating paratonia of patients having moderate to severe dementia, particularly of paratonia patients having severe or late stage dementia, and more particularly of patients with dementia and paratonia that experience involuntary postures that interfere in the ability to provide care and/or cause patient suffering.

"Dementia" within the meaning of the present invention may also diagnosed using the Global Deterioration Scale (GDS) of Reisberg (Reisberg et al., Am. J. Psych. 1982, 139:1136-1139), wherein dementia may be characterized by a GDS score of ≤6. However, within the present invention, the GDS scale is more typically used to assess or classify the severity of dementia (7-point scale). The GDS rates cognitive deterioration in dementia, from normal cognition (stage 1) to very severe cognitive decline (stage 7). Herein, a GDS score of 3 and 4 is considered as mild dementia, a GDS score of 5 as moderate dementia, and a GDS score of 6 or 7 as severe dementia.

In some embodiments, the present invention relates to the use of botulinum toxin in the treatment of paratonia in a patient suffering from dementia of severity staged 3 or 4 or higher, preferably 5 or higher, more preferably 6 or 7 on the GDS. This is generally correlated with when involuntary postures arise that interfere in provision of care and result in discomfort or other consequences of immobility.

The target patients or target patient group addressed by the botulinum toxin treatment according to the present invention may also be characterized by the Mini-Mental State Examination (MMSE) test (Folstein et al., J. Psych. Res. 1975, 12:189-198). This test is used to screen for cognitive impairment (MMSE scores range from 0 to 30). In accordance with the present invention, a patient with paratonia that is treated with botulinum toxin may have a MMSE score of 24 to 28 (i.e. very mild dementia), preferably a MMSE score of 19 to 23 (i.e. mild dementia), more preferably a MMSE score of 14 to 18 (i.e. moderately-severe), and most preferably a MMSE score of 13 or less or 10 or less (i.e. severe dementia).

While paratonia is seen in all types of dementia, the present invention relates, in some embodiments, to a botulinum toxin for use in the treatment of paratonia in a patient having cognitive impairment as a result of Alzheimer's disease (AD), vascular dementia (VaD), dementia with Lewy bodies (DLB), frontotemporal dementia (FTD), subcortical vascular dementia (SVD), or mixed dementia not otherwise specified (NOS).

In some embodiments, the botulinum toxin is used in the treatment of paratonia in a patient suffering from Alzheimer's disease. Said Alzheimer's disease may be diagnostically assessed as "probable Alzheimer's" according to the National Institute of Neurological and Communicative Disorders and Stroke/the Alzheimer's Disease and Related Disorders Associations (NINCDS-ADRDA) criteria, as known to a person skilled in the art.

The severity of said Alzheimer's disease may be in the range of moderate to severe, which corresponds to a score of 14 or less on the standardized Mini-Mental State Examination (MMSE; 0-30 scale) scale, and is, in some embodiments, severe Alzheimer's disease characterized by an MMSE score of less than 10. Said frontotemporal dementia (FTD) may be diagnosed according to consensus criteria described in Neary et al. (Neurology 1998, 51:1546-1554), and subcortical vascular dementia (SVD) according to the modified criteria from NINDS-AIREN (Erkinjuntti et al., J. Neural. Transm. Suppl. 2000, 59:23-30).

In accordance with the present invention, the botulinum toxin used is not particularly limited and is intended to refer to any forms and types of botulinum toxin. In particular, the botulinum toxin may be selected from botulinum toxin types A, B, $C_1$, D, E, F, G, or mixtures thereof. Also, the term "botulinum toxin", as used herein, is intended to include both the botulinum toxin complex (the "toxin complex") and the "neurotoxic component" of a botulinum toxin (or botulinum toxin complex).

As used herein, the term "(botulinum) toxin complex", refers to a high molecular weight complex comprising the neurotoxic component of approximately 150 kDa and, in addition, non-toxic proteins of Clostridium botulinum, including hemagglutinin and non-hemagglutinin proteins. In contrast, the term "neurotoxic component", as used herein, relates to the neurotoxic polypeptide of the toxin complex (the "150 kDa" polypeptide) without any associated non-toxic proteins. The botulinum toxin serotype A complex is commercially available, for example, as Botox® (Allergan, Inc.) or as Dysport® (Ipsen, Ltd.). The pure neurotoxic component is, for example, commercially available under the trade name Xeomin® (Merz Pharmaceuticals GmbH).

Furthermore, it is contemplated that the present also encompass isoforms, homologs, orthologs and paralogs of botulinum toxin that show at least 50%, at least 60%, at least 70%, at least 80%, at least 90% and up to 60%, up to 70%, up to 80%, up to 90%, up to 100% sequence identity to wild-type botulinum toxin, e.g. wild-type botulinum toxin A. The sequence identity can be calculated by any algorithm suitable to yield reliable results, for example by using the FASTA algorithm (W. R. Pearson & D. J. Lipman PNAS (1988) 85:2444-2448). Sequence identity may be calculated by comparing two polypeptides or two domains such as two LC domains or fragments thereof.

Modified and recombinant botulinum toxins are also within the scope of the present invention. With respect to suitable mutants, reference is made to WO 2006/027207, WO 2009/015840, WO 2006/114308, WO 2007/104567, WO 2010/022979, WO 2011/000929 and WO 2013/068476, which are all incorporated by reference herein. The present invention, however, also refers to botulinum toxins, which are chemically modified, e.g. by pegylation, glycosylation, sulfatation, phosphorylation or any other modification, in particular of one or more surface or solvent exposed amino acid(s). The modified, recombinant, isoforms, homologs, orthologs, paralogs and mutants suitable for use in the present invention are biologically active, i.e. able to translocate into neurons and cleave proteins of the SNARE complex (e.g. SNAP25), to exert its muscle paralyzing effects.

The biological activity may be tested, e.g., by a SNAP-25 protease assay, $LD_{50}$ assay, HDA assay, cell-based assay and the like. For example, any LC (light chain) domain, which shows proteolytic activity of more than 10%, 20%, 30%, 40%, 50%, 60%, 70%, 80%, 90% and up to 100% of the corresponding wild-type LC domain in a SNAP-25 assay is considered "biological active" or "to exhibit proteolytic activity" within the scope of this invention. Suitable SNAP25 assays include the "GFP-SNAP25 fluorescence release assay" (WO/2006/020748) or the "improved SNAP25 endopeptidase immuno-assay" (Jones et al., J. Immunol. Methods 2008, 329:92-101). Cell-based assays include the methods disclosed in WO2009/114748 or WO 2013/049508.

In a further aspect, the present invention relates to a method of treating paratonia in a patient, the method comprising locally administering a therapeutically effective amount of botulinum toxin to a muscle of the patient. This further aspect is closely related to the first aspect of the present invention and, thus, all comments, definitions and explanations given above in relation to the first aspect of the present invention, in particular with respect to paratonia, also apply to this further aspect. Likewise, all comments, definitions and explanations given below in relation to the further aspect of the present invention, in particular with regard to the administration mode or regimen, also apply to the first aspect.

The term "therapeutically effective amount", as used herein, refers to the amount of a botulinum toxin sufficient to effect beneficial or desired therapeutic results. The administered amount or dose of the botulinum toxin depends on the mode of application, the type of disease, the patient's weight, age, sex and state of health, and which muscles are chosen for injection depending on which posture causes a problem. Different muscles depending on their size generally require different dosing. A suitable dose may, in some embodiments, range from 10 to 700 U, preferably from 50 to 500 U, and more preferably from 100 to 350 U of botulinum toxin. As used herein, one "Unit" or "U" is the amount of botulinum toxin, which kills 50% of a specified mouse population after intraperitoneal injection, i.e. the mouse i.p. $LD_{50}$ (Schantz & Kauter, 1978). The terms "Units" or "U" are interchangeably with the term "MU" or "Mouse Units".

Administration can be single or multiple, as required. In some embodiments, if the (pure) neurotoxic component of a botulinum toxin is used, administration may be more frequent, for example every 4, 6, 8, 10 or 12 weeks. A therapeutically effective amount can be administered in one or more administrations, applications or dosages and is not intended to be limited to a particular formulation or administration route.

Within the present invention, the botulinum toxin is typically administered by local injection into a muscle of a patient. The term "patient", as used herein, generally relates to a human afflicted with paratonia. "Patient" may be interchangeably used herein with "subject" or "individual", and is also intended to have the same meaning as "people" having or suffering from or afflicted with paratonia. The muscle may be selected from, but is not limited to, biceps brachii, brachioradialis, pectoralis major, flexor digitorum superficialis, flexor digitorum profundis, flexor pollicis longus, triceps, lumbricals, flexor carpi ulnaris, and opponens pollicis. The administration is not limited to any particular administration regimen, mode, form, dose and interval. Usually, the botulinum toxin is administered by local intramuscular injection.

In some embodiments, the botulinum toxin is administered, e.g. by local injection, in the form of a liquid composition. This liquid composition comprises, in addition to botulinum toxin, at least one pharmaceutically acceptable carrier. The term "comprise", as used herein, is intended to encompass both the open-ended term "include" and the closed term "consist (of)". The term "pharmaceutically acceptable", as used herein, refers to those compounds or substances which are suitable for contact with the tissues of mammals, especially humans. The term "carrier", as used herein, relates to diluents or vehicles needed, required or desired in a composition suited for the intended purpose, such as intramuscular injection. Typically, the carrier is water or a physiological acceptable buffer solution.

In addition, the composition may comprise various other substances, for example stabilizing proteins (e.g., albumin, gelatin), sugars, carbohydrate polymers, polyols (e.g. glycerol, sorbitol), amino acids, vitamins (e.g. vitamin C), zinc, magnesium, anesthetic agents (e.g., local anesthetic agents like lidocaine), surfactants, tonicity modifiers, and the like.

In some embodiments, the composition comprises the (pure) neurotoxic component and one or more of the optional substances or components mentioned above, wherein the composition is devoid of any other protein component of the *clostridium botulinum* toxin complex.

The present invention will now be further illustrated by the following, non-limiting example.

EXAMPLE

The study presented below provides evidence that botulinum toxin treatment is capable of reducing involuntary postures and caregiver burden in elderly patients with cognitive impairment (dementia). In particular, the toxin treatment was found to produce significant improvement in the caregiver burden scale (CBS), the primary outcome measure of the study, and increase range of motion around a joint (Passive Range of Motion; PROM).

Overall, the results obtained suggest that administration of botulinum toxin in elderly people requiring full care as a result of dementia-associated paratonia provides a promising treatment strategy to efficiently and safely improve the patient's quality of live and reduce caregiver burden, and reduce consequences of immobility like skin breakdown, infection, and pressure sores amongst others.

Methods

Subjects

The study began on January 2011 and ended March 2013. Subjects were eligible for the study if they had severe cognitive impairment as a result of Alzheimer's disease (AD), vascular dementia (VaD), frontotemporal dementia (FTD), or mixed dementia not otherwise specified (NOS), and a score of >3 on the paratonia assessment instrument (PAI) (Hobbelen et al., Int. Psychoger. 2008, 20:840-852) with consequent paratonic rigidity in an arm(s) interfering in the provision of care. Exclusion criteria included alternate etiologies for increased tone such as parkinsonian syndromes manifesting rigidity or dystonia, known strokes or other focal neurological deficits, fixed contractures of the affected limb (assessed clinically as no mobility on passive range of motion), or injection with Botulinum toxin in the preceding 6 months. The study was approved by the Ethics Review Board at Baycrest Center for Geriatric Care. All subjects had written informed consent provided by their power of attorney (POA).

Study Design

Figure 1:
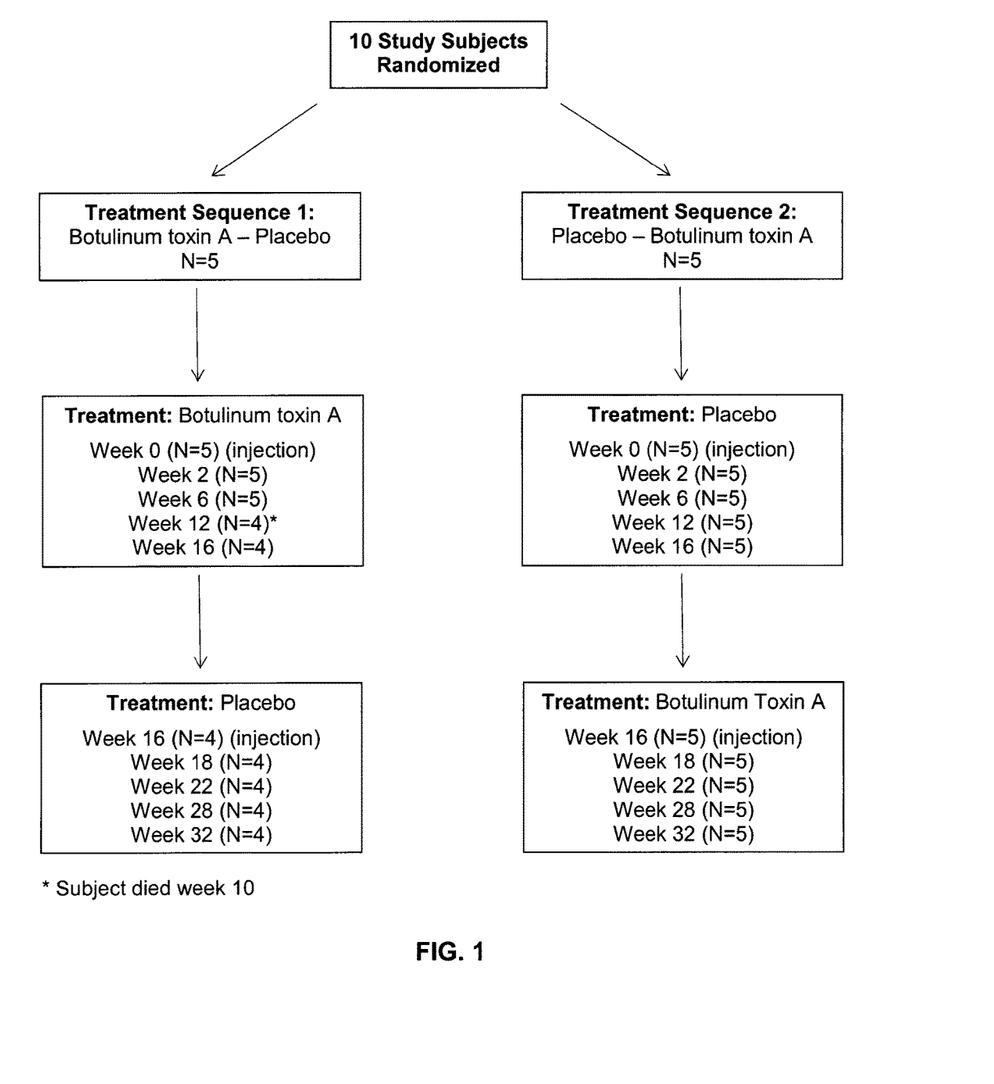
FIG. 1 is a flow diagram schematically showing the study design of the single center, double blind, placebo-controlled, crossover trial with two treatment cycles of 16 weeks each.

The study was a single center, randomized, double-blind, placebo-controlled, cross-over trial with two treatment cycles of 16 weeks each (total 32 weeks) (see FIG. 1). Following baseline assessments and injections at 0 and 16 weeks, assessments took place at 2, 6 and 12 weeks following injections. As this was a crossover design, each subject received both active drug and placebo with order of treatment allocation being randomized.

Muscles and doses chosen for injection were based on characteristics of the posture causing disability (i.e. magnitude of elbow flexion, shoulder abduction, finger flexion, etc.), and size of the muscle chosen for injection. Subjects were randomly assigned to receive up to 300 U of incobotulinumtoxinA (Xeomin®, Merz Pharmaceuticals GmbH; commercial lots 150070 and 154617) diluted with 0.9% saline to a concentration of 100 U/ml, or placebo (0.9% saline). Doses administered to each muscle were consistent with doses used in spasticity studies. The placebo and active drug were identical in packaging and appearance. Injection sites within the muscle were determined according to surface landmarks for motor end points as specified in a standard textbook of neuroanatomy (Delagi et al., Anatomic Guides for the Elecromyographer. Springfield, Ill.: Charles C. Thomas, 1980). Electromyography was used to confirm increased muscle activity.

Outcome Measures

Primary outcome measure was the caregiver burden scale (CBS), with secondary outcome measures including passive range of motion (PROM), global assessment scale (GAS), visual analogue scale (VAS), and pain assessment in advanced dementia (PAINAD).

Primary Outcome

Caregiver Burden Scale (CBS)

At baseline and at 2, 6, 12, 16, 18, 22, 28, and 32 weeks, caregiver burden was rated using the Caregiver Burden Scale (CBS), a functional scale that addresses cleaning the palm, cutting fingernails, dressing, and cleaning under the armpit. It uses a 5 point Likert scale from 0 (no difficulty) to 4 (cannot do the task) and then the score for each item is summed to result in a total CBS score (0-16) (Bhakta et al., J. Neurol., Neurosurg. and Psych. 2000, 69:217-221).

As cutting fingernails was not consistently part of daily morning care in this population, it was omitted from the assessments. Each assessment was performed twice per assessment week and scores were averaged over two days.

Secondary Outcome Measures

Passive Range of Motion (PROM) (Joint Angle Measurement)

Given the fluctuating nature of paratonia, using the Modified Ashworth Scale (MAS) (Brashear et al., New Engl. J. Med. 2002, 347:395-400; Waardenberg et al., Nederlands Tijdschrift voor Fysiotherapie 1999, 102:30-35), a validated scale for increased tone due to spasticity, a static entity, is not suitable. Therefore, joint angle measurements reflecting range of motion were used as a surrogate measure for severity of paratonia.

Global Assessment Scale (GAS) and Visual Analogue Scale (VAS)

At each follow-up visit, the overall response to treatment was evaluated by caregivers using the Global Assessment Scale (GAS). This scale estimates global improvement or worsening of overall functional status compared to the pre-treatment status and has therefore no baseline measurements. It is anchored from −4=very marked worsening of symptoms to 0=unchanged to +4=complete abolishment of signs and symptoms (Ashford S. and Turner-Stokes L., Physiother. Res. Int. 2006, 11:24-34).

The Visual Analogue Scale (VAS) (Waltz C. and Lenz E., Measurement in Nursing Research, 2nd ed., Philadelphia: F. A. Davis, 1991), representing caregiver perception of ease of care, was completed by the professional caregiver. The VAS consists of a 100 mm line with anchors of 0 "giving care to the residents is very difficult" and 100 "giving care to the residents is very easy"; scores represent the measured distance between 0 and the mark made by the caregiver on the line.

Pain Assessment in Advanced Dementia (PAINAD)

The Pain Assessment in Advanced Dementia (PAINAD) instrument (Warden et al., JAMDA 2003, 4:9-15) was used to assess whether treatments reduce pain in patients when having morning care performed. The PAINAD scale consists of 5 items (breathing, negative vocalization, facial expression, body language, and consolability) scored on a 0-2 point scale and then summed to arrive at a total score. This score was averaged over two days of assessments/week. Study personnel recorded the PAINAD score while observing morning care administered by the professional caregiver.

Safety

The study investigators assessed adverse events at each assessment. A serious adverse event was defined as an event that was fatal, life-threatening, disabling or required hospitalization. An adverse event was any event that was reported by the study subject's caregivers.

Statistical Analysis

In this study, 10 subjects were chosen a priori, which provided statistical power of 70-80% to detect mean changes between 0.5-1.5 points on a 5 point Likert scale between baseline and 6 weeks under different standard deviation assumptions (SD 0.5, 1, 1.5, or 2). This allowed for the detection of clinically meaningful changes in measurement with treatment even with a relatively small sample size.

While analysis of variance (ANOVA) is often used for the analysis of crossover trial data, mixed modeling techniques were used in this study in order to utilize all available information collected on study subjects during intervention and control periods. Mixed modeling was also used to address between-study heterogeneity within and between patients regarding paratonia severity, doses injected, what muscles were injected, and caregiver variability, through the introduction of patient-specific random effects (i.e., random intercepts). Treatment effect was assumed present by 6 weeks post-injection consistent with other studies.

The likelihood-ratio test was used to determine whether treating subjects as a random effect was necessary, and the Bayesian information criterion was calculated to help determine model fit. ANOVA was utilized to assess the efficacy of treatment with consideration of patient factors, sequence, sequence-by-treatment interaction, period, and period-by-treatment interaction effects. To account for the fluctuating nature of paratonia severity, measurements were performed twice (over a period of two days) with mean values from the two measurements used to assess outcomes. This provided an opportunity to evaluate reliability of measures, which was performed through calculation of intra-class correlation coefficients.

Results

Subjects

Ten subjects were enrolled in the study. Subject baseline demographic information is included in Table 1. Subjects were randomly allocated to each treatment sequence. There were no significant differences in the characteristics of the subjects in the two treatment sequence allocations (see Table 2). One subject in the Botulinum toxin-placebo sequence (Subject 4) died during week 10 of the study. Data on this subject was only collected and included up to Week 6.

TABLE 1

Subject demographics

| Subject | Age [yrs] | Gender [M/F] | Diagnosis | Disease Duration [yrs] | PAI | Total Toxin† Dose [U/ml] |
|---|---|---|---|---|---|---|
| 1 | 84 | F | AD* | 9 | 3 | 200 |
| 2 | 96 | F | AD | 11 | 4 | 300 |
| 3 | 86 | F | FTD§ | 5 | 2 | 300 |
| 4 | 88 | F | AD | 11 | 3 | 300 |
| 5 | 76 | F | AD | 8 | 3 | 240 |
| 6 | 93 | M | AD | 8 | 3 | 300 |
| 7 | 88 | F | AD | 8 | 3 | 175 |
| 8 | 69 | F | AD | 6 | 3 | 300 |
| 9 | 89 | F | AD | 12 | 3 | 175 |
| 10 | 85 | F | AD | 10 | 3 | 300 |
| Mean ± SD | 85.30 ± 8.00 | | | 8.80 ± 2.25 | 3 ± 0.47 | 259 ± 55.82 |

*AD = Alzheimer's disease
§FTD = frontotemporal dementia
†Toxin = incobotulinumtoxinA

TABLE 2

Subject characteristics by treatment allocation

| Characteristic | Sequence 1 (Placebo – IncoBTA*) (n = 5) | Sequence 2 (IncoBTA* – Placebo) (n = 5) | P value |
|---|---|---|---|
| Age | | | |
| Mean (year) ± Standard Deviation | 84.6 (range 69-96) | 86.0 (range 75-93) | P = 0.800 |
| Gender | | | |
| Male (n) | 0 | 1 | P = 0.347 |
| Female (n) | 5 | 4 | |

TABLE 2-continued

Subject characteristics by treatment allocation

| Characteristic | Sequence 1 (Placebo – IncoBTA*) (n = 5) | Sequence 2 (IncoBTA* – Placebo) (n = 5) | P value |
|---|---|---|---|
| Diagnosis | | | |
| AD (n) | 5 | 4 | P = 0.347 |
| FTD (n) | 0 | 1 | |
| Disease Duration | | | |
| Mean (yr) ± Standard Deviation | 9.60 ± 2.30 | 8.00 ± 2.12 | P = 0.286 |
| PAI | | | |
| Mean ± Standard Deviation | 3.20 ± 0.45 | 2.80 ± 0.45 | P = 0.195 |
| CBS-Total (Baseline) | | | |
| Mean ± Standard Deviation | 1.50 ± 0.15 | 1.93 ± 0.27 | P = 0.209 |
| Total Inco-BTA dose | | | |
| Mean [U/ml] ± Standard Deviation | 255.00 ± 62.25 | 263.00 ± 55.63 | P = 0.836 |

*IncobotulinumtoxinA

Doses and Injections

The distribution and doses of incobotulinumtoxinA injected are presented in Table 3.

TABLE 3

Muscles and doses injected

| Muscle | IncobotulinumtoxinA Units (U) Median (min, max) | Patients Injected n (%) |
|---|---|---|
| Biceps brachii | 50 (25, 100) | 10 (100%) |
| Brachioradialis | 45 (25, 100) | 5 (50%) |
| Pectoralis major | 90 (50, 125) | 8 (80%) |
| Flexor digitorum superficialis | 75 (50, 90) | 7 (70%) |
| Flexor digitorum profundis | 35 (20, 50) | 2 (20%) |
| Flexor pollicis longus | 15 (10, 25) | 3 (30%) |
| Triceps | 50 (25, 50) | 6 (60%) |
| Lumbricals | 35 (30, 40) | 2 (20%) |
| Flexor carpi ulnaris | 25 (25, 25) | 1 (10%) |
| Opponens pollicis | 17.5 (15, 20) | 2 (20%) |

Primary Outcome
Caregiver Burden

Figure 2:
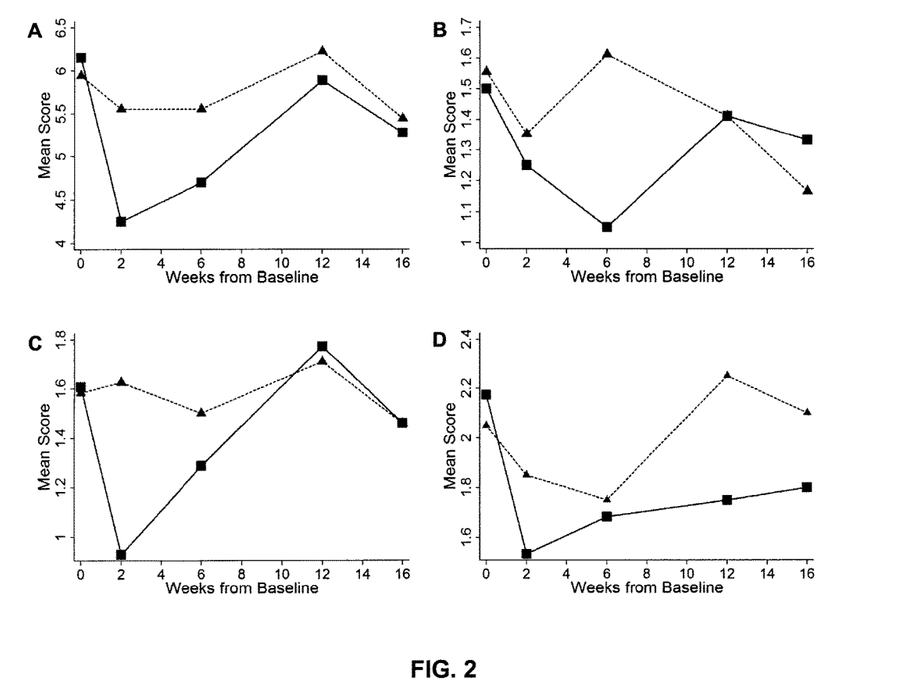
FIG. 2 is a graph showing the mean Caregiver Burden Scale (CBS) scores in subjects treated with incobotulinumtoxinA (■) and placebo (▲) as a function of time. A: Overall CBS scores. B: Dressing CBS subscores. C: Cleaning under the (left and right) armpit CBS subscores. D: Cleaning the (left and right) palm CBS subscores.

Graphical evaluation of CBS scores identified reduced (improved) mean total scores and sub-scores during the interval 2 to 6 weeks (peak effect) following injection with incobotulinumtoxinA (see FIG. 2). Mixed effects regression models evaluating treatment effects from 2 to 6 weeks post-injection identified a significant incobotulinumtoxinA treatment effect for most outcomes including CBS (see Table 4).

TABLE 4

Mixed model outcomes of CBS, PROM, PAINAS, GAS and VAS at two and six weeks after treatment with incobotulinumtoxinA

| Outcome Measure | N | Treatment Effect (95% CI) | P value |
|---|---|---|---|
| Caregiver Burden Scale (CBS) | | | |
| Total score | 10 | −1.11 (−2.04 to −0.18) | 0.02 |
| Dressing | 10 | −0.36 (−0.59 to −0.12) | 0.004 |
| Cleaning under arm (left) | 7 | −0.50 (−0.96 to −0.04) | 0.034 |
| Cleaning under arm (right) | 7 | −0.41 (−0.79 to −0.04) | 0.030 |
| Cleaning palm (left) | 5 | −0.25 (−0.78 to 0.28) | 0.4 |
| Cleaning palm (right) | 6 | −0.05 (−0.47 to 0.38) | 0.8 |
| Passive Range of Motion (PROM) | | | |
| Elbow extension (left) | 6 | 27.67 (13.32 to 42.02) | <0.001 |
| Elbow extension (right) | 8 | 22.07 (9.76 to 34.39) | <0.001 |
| Elbow flexion (left) | 4 | 9.94 (−0.32 to 20.19) | 0.06 |
| Elbow flexion (right) | 2 | −5.81 (−16.23 to 4.61) | 0.3 |
| Finger extension (left) | 5 | 19.85 (3.25 to 36.45) | 0.02 |
| Finger extension (right) | 6 | 23.56 (3.46 to 43.67) | 0.02 |
| Shoulder abduction (left) | 7 | 11.92 (5.46 to 18.38) | <0.001 |
| Shoulder abduction (right) | 7 | 8.58 (3.73 to 13.43) | 0.001 |
| Thumb abduction/extension (left) | 3 | 17.75 (−0.79 to 36.29) | 0.06 |
| Thumb abduction/extension (right) | 2 | −0.50 (−9.68 to 8.68) | 0.9 |
| Other Secondary Measures | | | |
| Pain Assessment in Advanced Dementia Scale (PAINAD) | 10 | −0.09 (−0.70 to 0.51) | 0.8 |
| Global Assessment Scale (GAS) | 10 | 0.53 (−0.07 to 1.13) | 0.008 |
| Visual Analogue Scale (VAS) | 10 | 5.30 (−4.64 to 15.23) | 0.3 |

Botulinum toxin reduced overall CBS score by 1.11 ($p=0.02$); dressing subscores were reduced by 0.36 ($p=0.004$); and scores for cleaning under the left and right armpits were reduced by 0.50 ($p=0.03$), 0.41 ($p=0.03$). There was reduction in cleaning of the left and right palms of the hand 0.25 ($p=0.4$), and 0.05 ($p=0.8$) but this did not reach level of significance. By contrast, ANOVA comparing baseline to 6 week effects found no significant differences between treatment and placebo in CBS total score ($p=0.2$), though significant improvement was present in the dressing component of the CBS ($p=0.01$). No period or sequence effects were detected. Models fits were improved without substantial loss of parsimony with the incorporation of subject random effects, as demonstrated by reductions in the Bayesian information criterion, suggesting that between-individual heterogeneity in disease and response was an important consideration in explaining Botulinum toxin treatment effects.

Figure 3:
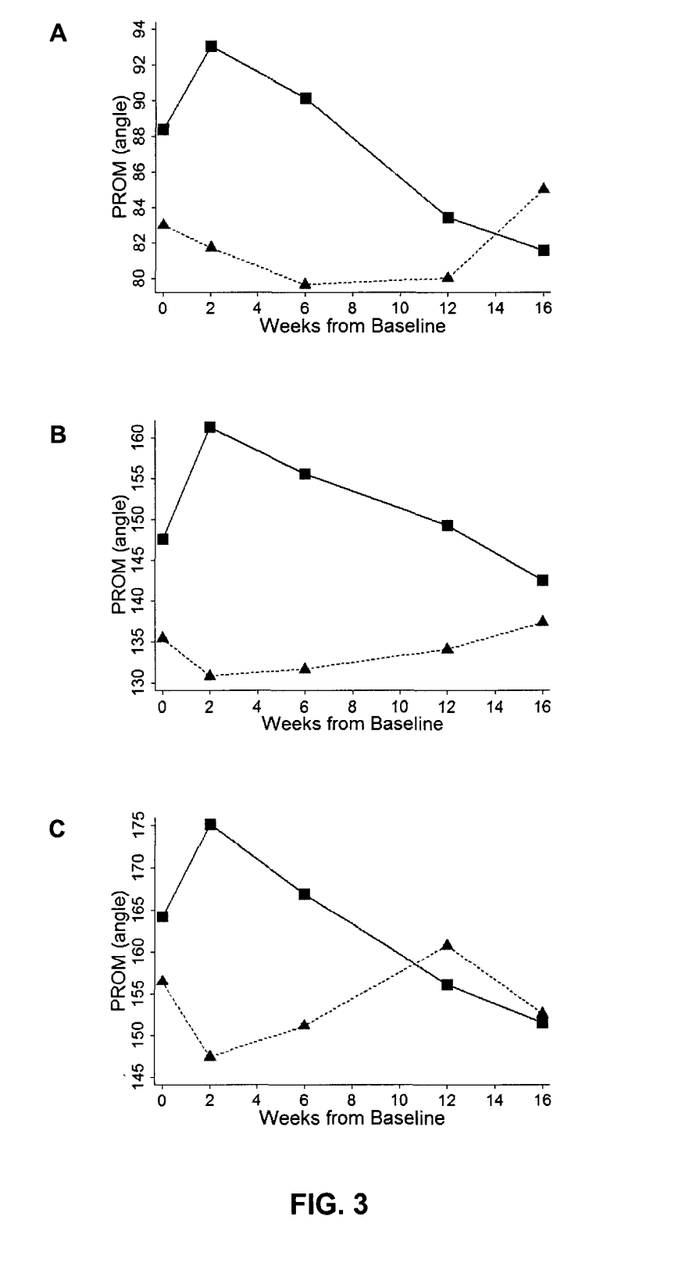
FIG. 3 is a graph showing the Passive Range of Motion (PROM) as represented by increased joint angles following treatment with incobotulinumtoxinA (■) and placebo (▲) as a function of time. A: PROM of shoulder abduction. B: PROM of (left and right) elbow extension. C: PROM of (left and right) fingers extension.

With respect to secondary outcomes, significant improvement in passive range of motion (PROM) as represented by increased joint angles was detected for most joints with mixed effects models (see FIG. 3): Left and right elbow extension increased by 27.67 degrees ($p<0.001$) and 22.07 degrees ($p<0.001$), while left and right finger extension increased by 19.85 degrees ($p=0.02$) and 23.56 degrees ($p=0.02$). Improvements were also seen in the left and right shoulder abduction by 11.92 degrees ($p<0.001$) and 8.58 degrees ($p=0.001$). No significant treatment effects were found for GAS, VAS, or PAINAD.

Reliability

All measures used in this study appeared reliable based on estimation of intra-class correlation coefficients (ICC). ICC were high for the CBS, with near-perfect reproducibility for both the total score and dressing component score between day 1 and day 2 of assessments. Cleaning scores, joint angle measurements, GAS, VAS, and PAINAD also demonstrated good reliability (see Table 5).

TABLE 5

Reliability based on estimation of ICC

| OUTCOME MEASURE | N | ICC |
|---|---|---|
| CAREGIVER BURDEN SCALE (CBS) | | |
| Total Score | 10 | 0.935 |
| Dressing | 10 | 0.918 |
| Cleaning under arm (left) | 7 | 0.859 |
| Cleaning under arm (right) | 7 | 0.814 |
| Cleaning palm (left) | 5 | 0.819 |
| Cleaning palm (left) | 6 | 0.893 |
| PASSIVE RANGE OF MOTION (PROM) | | |
| Elbow extension (left) | 6 | 0.955 |
| Elbow extension (right) | 8 | 0.829 |
| Elbow flexion (left) | 4 | 0.925 |
| Elbow flexion (right) | 2 | 0.820 |
| Finger extension (left) | 5 | 0.803 |
| Finger extension (right) | 6 | 0.691 |
| Shoulder abduction (left) | 7 | 0.900 |
| Shoulder abduction (right) | 7 | 0.920 |
| Thumb abduction/extension (left) | 3 | 0.937 |
| Thumb abduction/extension (right) | 2 | 0.716 |
| OTHER SECONDARY MEASURES | | |
| Pain Assessment in Advanced Dementia Scale (PAINAD) | 10 | 0.927 |
| Global Assessment Scale (GAS) | 10 | 0.826 |
| Visual Analogue Scale (VAS) | 10 | 0.845 |

Safety

There were no adverse effects reported by the caregivers of the study participants. One subject (Subject 4) died 10 weeks following the first set of injections (treatment arm).

The subject died of natural causes. This was deemed unrelated to incobotulinum toxin injections.

In summary, the results presented above suggest that in cognitively impaired individuals with increased muscle tone due to paratonia, Botulinum toxin A is a safe intervention which provides meaningful reduction of caregiver burden by reducing tone and increasing range of movement in affected limbs. Strong treatment effects were already present 2 weeks after injection, and remained strong until 6 weeks.

The potential to impact caregiver burden is an important health and health-economic objective. In people with advanced cognitive impairment and total dependence on caregivers for all aspects of care, caregiver burden has been demonstrated to be a strong predictor of health-related quality of life (Dowding et al., Drugs & Aging 2006, 23:693-721).

There has been concern that known risks such as swallowing impairment or breathing difficulties would be enhanced in this population, but in this study we did not identify adverse events. The single fatality during the trial occurred in an 88 year-old individual and careful investigation revealed no relationship between this death and Botulinum toxin therapy.

In conclusion, the present study shows that patients with paratonic rigidity experience benefit from administration of Botulinum toxin, which should facilitate provision of care by preserving range of motion. In a randomized, double-blind, placebo controlled trial described above, clinically and statistically significant effects on caregiver burden were found, and it is anticipated that the use of Botulinum toxin would also provide downstream benefits through delay or prevention of contractures. Thus, botulinum toxin therapy of paratonia has the potential to improve the health-related quality of life in dependent, cognitively impaired individuals and their caregivers. Given the rising economic and social burden of dementia, the above results are promising.

The invention claimed is:

1. A method of treating a patient having paratonia comprising: administering to the patient an effective amount of a botulinum toxin.

2. The method of claim 1, wherein the patient has been diagnosed to have a PAI (paratonia assessment instrument) score of ≥3.

3. The method of claim 1, wherein the paratonia affects an upper and/or lower limb of the patient.

4. The method of claim 1, wherein the paratonia is associated with cognitive impairment as a result of Alzheimer's disease (AD), vascular dementia (VaD), dementia with Lewy bodies (DLB), frontotemporal dementia (FTD), subcortical vascular dementia (SVD), or mixed dementia not otherwise specified (NOS).

5. The method of claim 1, wherein the administering comprises locally administering the botulinum toxin by intramuscular injection.

6. The method of claim 1, wherein the effective amount is an amount of about 10 to 700 Units.

7. The method of claim 1, wherein the botulinum toxin is selected from the group consisting of botulinum toxin types A, B, $C_1$, D, E, F, G, and mixtures thereof.

8. The method of claim 7, wherein the botulinum toxin is botulinum toxin type A.

9. The method of claim 1, wherein the botulinum toxin is a botulinum toxin complex or the neurotoxic component of a botulinum toxin complex.

10. A method of treating paratonia in a patient, the method comprising locally administering a therapeutically effective amount of botulinum toxin to a muscle of the patient.

11. The method of claim 10, wherein the muscle of the patient is in an upper or lower limb of the patient.

12. The method of claim 11, wherein the paratonia affects the upper or lower limb of the patient.

13. The method of claim 10, wherein the patient has been diagnosed to have a PAI (paratonia assessment instrument) score of 3.

14. The method of claim 10, wherein the paratonia is associated with cognitive impairment as a result of Alzheimer's disease (AD), vascular dementia (VaD), dementia with Lewy bodies (DLB), frontotemporal dementia (FTD), subcortical vascular dementia (SVD), or mixed dementia not otherwise specified (NOS).

15. The method of claim 10, wherein the therapeutically effective amount is an amount of about 10 to 700 Units.

16. The method of claim 10, wherein the botulinum toxin is selected from the group consisting of botulinum toxin types A, B, $C_1$, D, E, F, G, and mixtures thereof.

17. The method of claim 16, wherein the botulinum toxin is botulinum toxin type A.

18. The method of claim 10, wherein the botulinum toxin is a botulinum toxin complex or the neurotoxic component of a botulinum toxin complex.

* * * * *